US009808194B2

(12) United States Patent
Bhat et al.

(10) Patent No.: US 9,808,194 B2
(45) Date of Patent: Nov. 7, 2017

(54) CUSHIONING SUPPORT FOR MONITORING USER ACTIVITY

(71) Applicant: PRS Medical Technologies, Inc., Menlo Park, CA (US)

(72) Inventors: Nikhil Bhat, Fremont, CA (US); Allen J. Li, San Francisco, CA (US); George Y. Choi, Menlo Park, CA (US); Colin Choi, Menlo Park, CA (US)

(73) Assignee: PRS Medical Technologies, Inc., Menlo Park, CA (US)

( * ) Notice: Subject to any disclaimer, the term of this patent is extended or adjusted under 35 U.S.C. 154(b) by 0 days.

(21) Appl. No.: 14/849,358

(22) Filed: Sep. 9, 2015

(65) Prior Publication Data

US 2016/0128623 A1    May 12, 2016

Related U.S. Application Data

(60) Provisional application No. 62/055,356, filed on Sep. 25, 2014.

(51) Int. Cl.
| | |
|---|---|
| *A61B 5/00* | (2006.01) |
| *A61B 5/0205* | (2006.01) |
| *A61B 5/103* | (2006.01) |
| *G01G 19/44* | (2006.01) |

(52) U.S. Cl.
CPC ............ *A61B 5/447* (2013.01); *A61B 5/0022* (2013.01); *A61B 5/1036* (2013.01); *A61B 5/6892* (2013.01); *A61B 5/746* (2013.01); *A61B 5/0004* (2013.01); *A61B 5/0205* (2013.01); *A61B 2562/0247* (2013.01); *G01G 19/44* (2013.01)

(58) Field of Classification Search
CPC ...... G01G 19/44; A61B 5/746; A61B 5/6892; A61B 5/0022; A61B 5/1036; A61B 5/0205; A61B 5/0004
See application file for complete search history.

(56) References Cited

U.S. PATENT DOCUMENTS

| | | | | |
|---|---|---|---|---|
| 6,041,658 | A * | 3/2000 | Casey | B60N 2/002 177/136 |
| 6,206,474 | B1 * | 3/2001 | Kruse | B60N 2/70 297/284.3 |
| 6,966,233 | B2 * | 11/2005 | Brown | G01G 19/4142 73/862.581 |
| 7,026,940 | B2 | 4/2006 | Cherubini | |
| 8,151,654 | B2 * | 4/2012 | Speckhart | B60N 2/002 73/862.454 |
| 8,325,934 | B2 | 12/2012 | Kuo | |
| 8,477,039 | B2 | 7/2013 | Gleckler et al. | |

(Continued)

*Primary Examiner* — Michael C Stout
(74) *Attorney, Agent, or Firm* — Levine Bagade Han LLP

(57) ABSTRACT

Multi-layer cushion supports are described which may generally comprise a first support having a first contact surface for contacting a portion of a body and a second surface opposite to the first surface, the first support defining a central chamber and a peripheral chamber surrounding the central chamber, wherein the first support is filled with a first gas or liquid and a second support attached to the first support along the first contact surface. The second support may be filled with a second gas or liquid which is relatively more viscous than the first gas or liquid. In particular, the first support may be filled with a volume of air and the second support may be filled with oil which is less than the volume of air.

39 Claims, 10 Drawing Sheets

(56) References Cited

U.S. PATENT DOCUMENTS

| | | | |
|---|---|---|---|
| 2003/0067149 A1* | 4/2003 | Gray | B60R 21/01516 280/735 |
| 2004/0086681 A1* | 5/2004 | Wang | A43B 7/144 428/76 |
| 2008/0109964 A1* | 5/2008 | Flocard | A61B 5/6891 5/713 |
| 2009/0058661 A1* | 3/2009 | Gleckler | A61B 5/103 340/573.7 |
| 2009/0177121 A1 | 7/2009 | Brandon et al. | |
| 2010/0268122 A1* | 10/2010 | Drennan | A61B 5/103 600/587 |
| 2011/0068939 A1* | 3/2011 | Lachenbruch | A61B 5/002 340/626 |
| 2011/0144455 A1* | 6/2011 | Young | A61B 5/0205 600/301 |
| 2011/0239372 A1 | 10/2011 | Bhat et al. | |
| 2011/0245732 A1* | 10/2011 | Mravyan | A61B 5/1116 600/587 |
| 2011/0263950 A1* | 10/2011 | Larson | A61B 5/1113 600/301 |
| 2011/0275939 A1* | 11/2011 | Walsh | A61B 5/4561 600/473 |
| 2011/0302719 A1* | 12/2011 | Schwirian | A61B 5/1115 5/706 |
| 2013/0012786 A1* | 1/2013 | Horseman | G06F 19/3418 600/301 |
| 2013/0019873 A1 | 1/2013 | Choi et al. | |
| 2013/0019881 A1 | 1/2013 | Bhat et al. | |
| 2013/0043988 A1 | 2/2013 | Bruno | |
| 2013/0092175 A1 | 4/2013 | Bhat et al. | |
| 2013/0112213 A1 | 5/2013 | Bhat et al. | |
| 2013/0174855 A1 | 7/2013 | Choi et al. | |
| 2013/0174856 A1 | 7/2013 | Choi et al. | |
| 2013/0174859 A1 | 7/2013 | Bhat et al. | |
| 2013/0180530 A1 | 7/2013 | Choi et al. | |
| 2013/0180531 A1 | 7/2013 | Choi et al. | |
| 2013/0298918 A1 | 11/2013 | Choi et al. | |
| 2015/0015399 A1* | 1/2015 | Gleckler | A61B 5/1116 340/573.7 |
| 2015/0025327 A1* | 1/2015 | Young | A61B 5/1115 600/301 |
| 2015/0052685 A1 | 2/2015 | Bhat et al. | |
| 2015/0331524 A1* | 11/2015 | McMillen | G01L 1/18 345/174 |
| 2016/0089083 A1* | 3/2016 | Sutton | A61B 5/6891 600/587 |

* cited by examiner

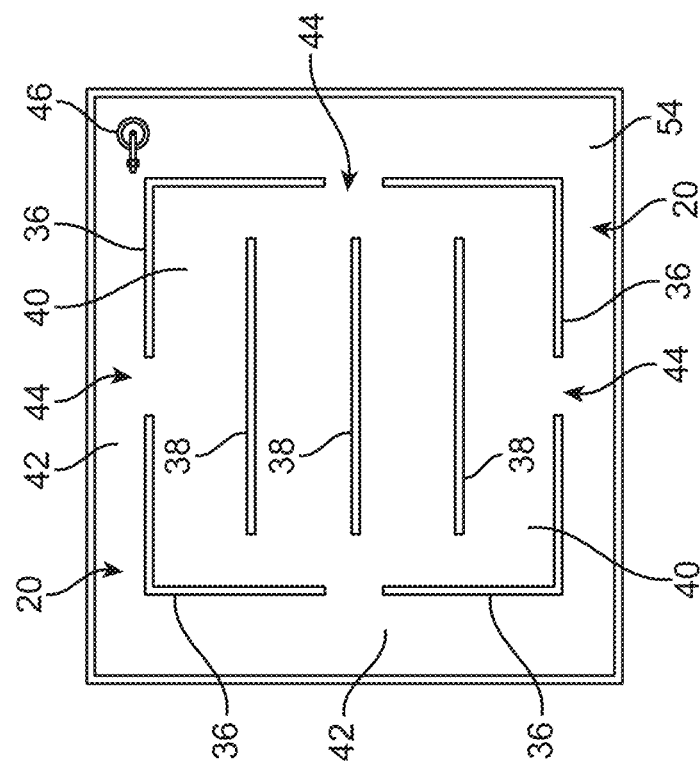
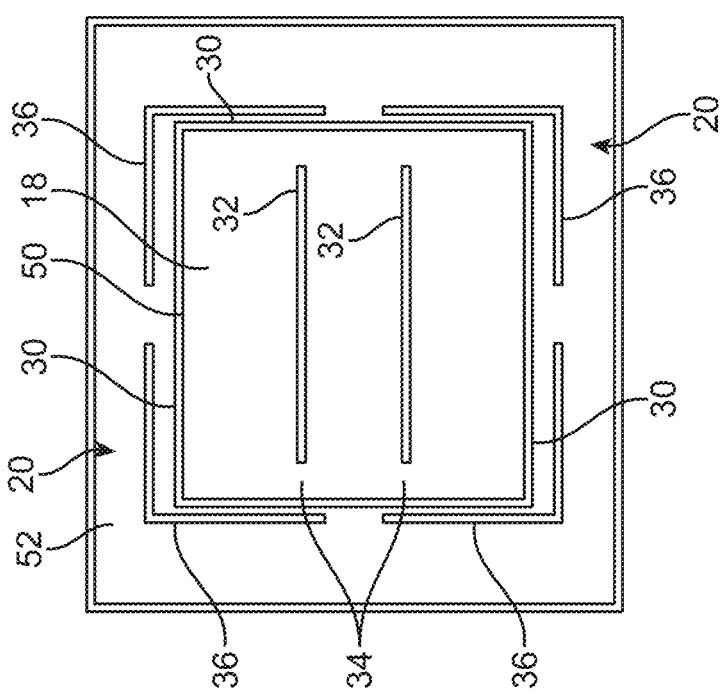
FIG. 4A
FIG. 4B

| Test | Mapping Reference |
|---|---|
| 1 (No cushon) | |
| 2 (Multi-layered support with 1.5 in. x 17 in. x 19 in. foam layer along bottom surface) | |
| 3 (Gel layer with foam layers along top and bottom surfaces) | |
| 4 (Multi-layered support with 0.5 in. x 17 in. x 19 in. foam layer along bottom surface) | |
| 5 (Multi-layered support with 0.5 in. x 17 in. x 19 in. foam layer along top surface) | |
| 6 (Multi-layered support with 0.5 in. x 17 in. x 19 in. foam along top and bottom surfaces) | |

FIG. 5

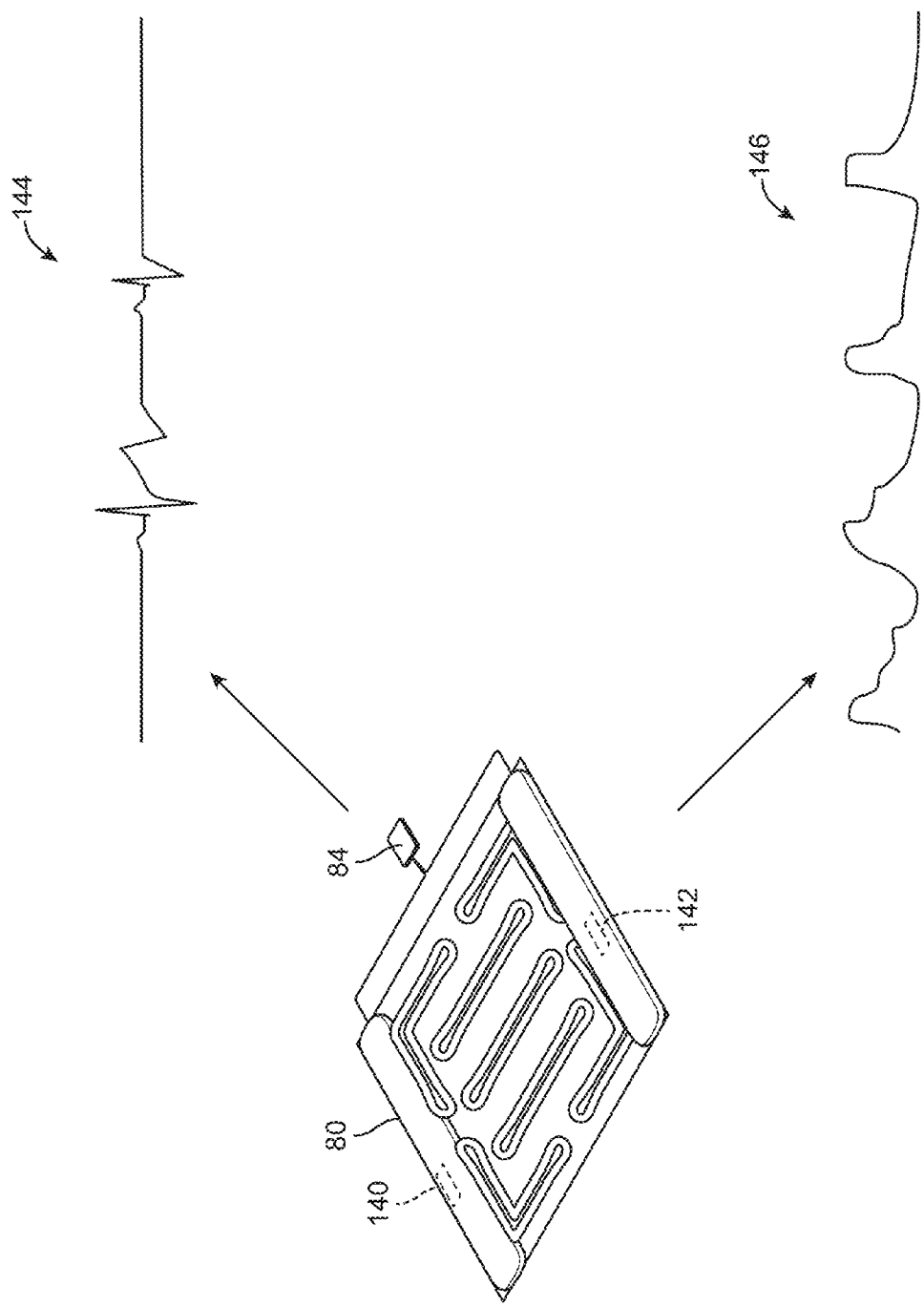

CUSHIONING SUPPORT FOR MONITORING USER ACTIVITY

CROSS-REFERENCE TO RELATED APPLICATIONS

This application claims the benefit of priority to U.S. Prov. App. 62/055,356 filed Sep. 25, 2014, which is incorporated herein by reference in its entirety.

FIELD OF THE INVENTION

The present invention relates to devices and methods for supporting portions of a patient's body and monitoring parameters of the user's activities. More particularly, the present invention relates to devices and methods for supporting portions of a patient's body such as for preventing and treating pressure ulcers with cushioning supports having multiple layers and monitoring parameters of the user such as sitting duration, posture, biometric data, etc.

BACKGROUND OF THE INVENTION

Individuals who are forced to sit or lie down for extended periods of time typically experience tissue necrosis over localized regions of their body known as decubitus ulcers or pressure sores. Pressure ulcers generally occur at locations of the body where the bony prominence is high and the underlying skin breaks down when constant pressure is placed against the skin. Blood circulation is inhibited or prevented in these localized areas and can even occur when the patient has been lying against or upon cushioning devices. Examples of areas of the body where pressure sores typically occur include the sacrum, greater trochanter, ischial tuberosity, malleolus, heel, etc. When pressure ulcers form, they can lead to extensive stays in the hospital or even to amputation.

Conventional cushioning devices generally utilize flexible materials such as foam or springs which allow for the cushion to deform and conform to the patient's body. While the cushioning device attempts to redistribute the loading from localized regions of the patient's body to a larger area over the rest of the body, such devices typically bottom out such that the patient's body contacts the underlying platform and nonetheless localizes the pressure onto the body.

Other cushioning devices have utilized fluid-filled cushions which consist of large single bladders or compartmentalized fluid or gas-filled bladders which inhibit fluid contained within the bladders from flowing laterally. In a fluid filled bladder disposed on a contoured seat, the fluid filled bladder typically bottoms out in one or more areas when supporting a patient's body weight. The places where the bladder bottoms out are sources of high localized pressure. Thus, such an assembly does not distribute pressure evenly across the portions of the anatomy in contact with the bladder. The amount of water that is used in such a bladder can be increased such that bottoming out does not occur. However, this design sacrifices stability. Additionally, since such cushions are typically designed to accommodate a wide range of patient populations, patients who are not as heavy as the maximum for which the cushion was designed for will suffer even more lack of stability than would be needed.

Another problem with simply increasing the amount of fluid to prevent bottoming out is that this requires significant volume of fluid beneath the patient and/or require specialized bedding. Additionally, many fluid filled membranes are too thick to provide adequate pressure relief because the hammocking that occurs in the regions of high protrusions. Thus, the suspension of the patient's body typically results in significantly non-uniform pressure application, with higher pressures being applied to protruding portions of the patient's body due to lack of adequate conformance of the bladder material to the patient's body.

Additionally, even with a supportive cushion, the user or patient interaction with the cushion may also need monitoring. For instance, the patient may lie upon the cushion for extended periods of time which are too long, or the patient may remain upon the cushion with an improper posture.

Accordingly, there exists a need for a cushioning device which may conform to regions of the user's body as well as monitor or track various parameters of the user's interaction with the cushioning device.

BRIEF SUMMARY OF THE INVENTION

A conformable support assembly may be configured to conform to particular regions of a patient's body where pressure ulcers tend to form, e.g., sacrum, trochanter, ischium, head, elbow, heel, as well as any other region of the body where support is desired. Such support is particularly desired when the patient sits, lies, or stands for an extended period of time such as sitting in a wheelchair.

In one variation, the multi-layer cushion support may generally comprise a first support having a first contact surface for contacting a portion of a body and a second surface opposite to the first surface, the first support defining a central chamber and a peripheral chamber surrounding the central chamber, wherein the first support is filled with a first gas or liquid and a second support attached to the first support along the first contact surface, wherein the second support is filled with a second gas or liquid which is relatively more viscous than the first gas or liquid. In particular, the first support may be filled with a volume of air and the second support may be filled with oil which is less than the volume of air.

Generally in use, the multi-layer cushion support may be used to support a portion of a patient's body by providing a multi-layer cushion support comprising a first support having a first contact surface and a second surface opposite to the first surface where the first support defines a central chamber and a peripheral chamber surrounding the central chamber, and a second support attached to the first support along the first contact surface, wherein the first support is filled with a first gas or liquid and the second support is filled with a second gas or liquid which is relatively more viscous than the first gas or liquid and positioning the second support adjacent to the portion of the body.

Various features which may be incorporated or included into the support assemblies described herein may be seen in further detail in the following U.S. patent application Ser. No. 13/189,320 filed Jul. 22, 2011 (U.S. Pub. 2013/0019873); Ser. No. 13/407,628 filed Feb. 28, 2012 (U.S. Pub. 2013/0019881); Ser. No. 13/683,198 filed Nov. 21, 2012 (U.S. Pub. 2013/0112213); Ser. No. 13/693,691 filed Dec. 4, 2012 (U.S. Pub. 2013/0092175); Ser. No. 13/760,482 filed Feb. 6, 2013 (U.S. Pub. 2013/0180530); Ser. No. 13/784,035 filed Mar. 4, 2013 (U.S. Pub. 2013/0180531); Ser. No. 13/784,133 filed Mar. 4, 2013 (U.S. Pub. 2013/0174855); Ser. No. 13/784,215 filed Mar. 4, 2013 (U.S. Pub. 2013/0174856); Ser. No. 13/784,260 filed Mar. 4, 2013 (U.S. Pub. 2013/0174859); Ser. No. 13/945,684 filed Jul. 18, 2013 (U.S. Pub. 2013/0298918); Ser. No. 13/065,877 filed Mar. 30, 2011 (U.S. Pub. 2011/0239372); Ser. No. 13/973,840 filed Aug. 22, 2013; and Ser. No. 14/191,212 filed Feb.

26, 2014. Each of which is incorporated herein by reference in its entirety and for any purpose herein.

A cushion support may have a multi-layered cushioning support contained within an enveloping cover. The multi-layered cushioning support may generally comprise several interconnected chambers configured to have a central support region and a surrounding support region which are in fluid communication with one another. The multi-layered support may be optionally filled with a gas (such as air) or liquid (such as water or mineral oil) or a combination of both. The multi-layered support may also be sized in various dimensions suitable for placement under a patient body, e.g., 18 in.×20 in. for use as a cushion such as on a wheelchair. The multi-layered support may also incorporate a relatively smaller secondary chamber formed by an additional layer attached (such as by welding) upon the surface of the central support region such that the region surrounds this secondary chamber. The secondary chamber may be filled by a volume of liquid, such as mineral oil, which is relatively more viscous than the gas or liquid filled within the central support region or surrounding support region. Moreover, this secondary chamber may remain fluidly disconnected from the central support region and the surrounding support region.

A cushioning foam layer may be positioned adjacent to the support provided that this cushioning foam layer is positioned along a bottom surface of the support, i.e., along a surface of the support opposite from the secondary chamber. This is to allow for the multi-layered support and secondary chamber to come into direct contact against the patient's body without any other materials interfering (aside from the cover). The cushioning foam layer may be comprised of, e.g., different density polyurethane foams, which can be fabricated into different sizes and thicknesses (e.g., 17 in.×19 in.×0.5 in.) depending upon the desired application. The foam layer can be alternatively replaced by other cushioning designs such as a gel-type material, biasing springs, etc.

The cover may envelope both the multi-layer support and the foam layer and may also be fabricated from various materials which can be breathable and waterproof. The surface of the cover may also be made to have, e.g., an anti-skid surface, over its entire surface or along selective surfaces such as the bottom surface in contact with a platform. The cover may be sized (e.g., 18 in.×20 in.×1.5 in.) similarly to the multi-layer support and foam layer which may both be inserted into the cover through an opening defined along one of the edges of the cover. Additionally, while the individual layers may be maintained in their relative positioning by various mechanisms such as straps, fasteners, adhesives, etc., their relative positioning may also be maintained by the cover. Also, while the cover may be placed atop the secondary chamber for direct contact against the patient's body, the cover is sufficiently thin enough so as not to interfere with the cushioning support provided the layers.

The cushioning foam layer is positioned along a bottom surface of the support, i.e., along a surface of the support opposite from the secondary chamber, so that the secondary chamber and multi-layer support may be positioned into direct contact through the cover, if present, against the patient's body. Having the secondary chamber of the support placed into contact against the patient's body allows for effective pressure distribution throughout the support while the foam positioned beneath the support (i.e., along the surface of the support opposite of the secondary chamber and away from the patient's body) provides for further cushioning support of the patient's body.

However, other variations of the cushioning support may include one example where the foam layer may be positioned atop the multi-layer support. In this variation, the foam layer may be positioned along the same surface of the secondary chamber such that the foam layer comes into contact through the cover with the patient's body.

Turning now to the multi-layer support, the secondary chamber may be formed atop the support via attachment along its edges which may be welded, adhered, or otherwise attached. While the secondary chamber may form a single chamber, one or more barriers or boundaries may be formed along the secondary chamber at least partially dividing the secondary chamber into one or more sub-chambers which are fluidly connected to one another. The inclusion of the barriers or boundaries may effectively slow or inhibit the flow of any fluids contained within the secondary chamber from shifting to quickly such as when the patient adjusts their body position upon the support.

Moreover, the secondary chamber may be formed to have an overall volume of, e.g., 0.6 liters, although this volume may be decreased or increased depending upon the desired results and the type of liquid contained within the chamber. This variation may contain, e.g., 0.6 liters of mineral oil, as the oil may help in reducing the pressure in combination with an underlying air layer contained within the remaining chamber of the support. When in use, the oil layer within the chamber may be cradled by the underlying air chamber to prevent any potential "edge effects" associated with fluid interfaces. Moreover, the inclusion of the oil layer within the chamber may also facilitate the delivery of cooling or heating therapy against the patient body as oil may be cooled or heated by any number of passive or active methods.

Variations of the multi-layered support described herein may be used for supporting other regions of the body. For instance, an embodiment for supportive use of the patient's heels may similarly utilize the same features. Such a variation may be designed to have dimensions scaled appropriately for supporting a heel (e.g., 10 to 13 in. width, 28 to 35 in. length, and 2 to 8 in. height) such that the support may be positioned below the calf when the patient is lying upon a bed so that the heel is lifted off the surface of the bed. The heel protector can also be designed to have an incline to give a gentle slope.

Additionally, the support may be integrated with one or more sensors and/or electronics which enable the support to communicate, for instance, with a remote device to allow for the monitoring of various parameters such as pressure, sitting duration, etc. or various physiological parameters of the user. The integrated sensing and/or monitoring of the support may thus be configured to sense specific parameters such as the user's sitting duration where the support and/or remote device may be configured to provide a warning or alert the user if duration is too long, i.e., at or above a predetermined sitting duration threshold.

Additionally and/or alternatively, the support and/or device can be configured to sense for improper posture of the user and to provide a warning or alert to the user if their posture needs correction. Additionally and/or alternatively, the support and/or device can also be configured to sense physiological parameters such as breathing rate, heart rate, etc., and to update the user on the biometrics.

Generally, one variation of the monitoring system may comprise a support for supporting at least a portion of a user's body, at least one pressure sensor in communication with the support, and an electronics unit in communication with the at least one pressure sensor, wherein the electronics unit is configured to transmit information relating to pressure sensed from the at least one pressure sensor to a remote device.

In use, one variation of a method of monitoring use of the support may generally comprise providing a support for supporting at least a portion of a user's body, sensing a pressure within the support via at least one pressure sensor when the portion of the user's body is positioned upon the support, and transmitting information relating to the pressure sensed by the at least one pressure sensor to a remote device via an electronics unit in communication with the at least one pressure sensor.

One example may include a support and a mobile device (e.g., smart phone, PDA, tablet, laptop, etc.) which is transportable and readily programmable (such as via an application, standard software, etc.) in communication with one another. The communication may occur via a wired cable or wirelessly through any number of wireless protocols (e.g., Bluetooth®, 802.11, GSM or CDMA cellular protocols, RF, NFC, etc.). Additionally and/or alternatively, communication may occur between the support and mobile device through the internet or other network (e.g., LAN, WAN, etc.).

In the event that the support and mobile device communicate through the internet, any or all of the monitored data (which may also be stored in local memory within the support) may be uploaded to a remote cloud storage location, if so desired. This data may be processed locally within the electronics integrated with the support or via the mobile device or a remote computer for display or tracking by the user. Optionally, the user's data as well as the data from multiple users may all be uploaded and compared for display to one or more the individual users. For instance, one individual user may create a group of other users authorized by this individual for sharing and comparing one another's data and/or for feedback by the group of users.

In one example for utilizing the sensor, the support may be used to track the duration of time that the user has been sitting upon or against the support and to optionally provide an alert either to the user or to a designated third party (e.g., relative, friend, care provider, doctor, nurse, etc.) via the mobile device (or another designated device) if the user has been sitting in one position for too long. Once the support is loaded with weight as is the case when the user sits on it, the pressure inside the bladder chamber increases. Typically the unloaded bladder may have an internal bladder pressure ranging from, e.g., 0 to 0.2 psi, and when a person of typical weight sits upon the support, the pressure may increase up to, e.g., 0.2 to 1 psi, depending on the weight of the person. This change in pressure is instantaneous.

The sensor may be connected to the fluid chamber of the bladder and this pressure reading is measured and converted into a voltage by the electronics unit. The sensor reading can be transmitted remotely via different wireless communication modes (as described herein) or wired communication to the mobile device.

Another variation of the system may include a support which may be configured to sense for improper posture by the user and to warn and/or alert the user if their posture needs correction. The support may have a fluid chamber which is separated into at least two separate chambers which are each in communication with its own respective pressure sensor. Each of the sensors may be connected via respective wires or cables to an electronics unit which may be used to monitor and process the data received from each of the sensors.

Regardless of the number of chambers and sensors, the sensors may be positioned on opposing sides of the support and at locations sufficiently distanced from one another so that the weight distribution of the user may be reflected by the different sensors to indicate differential loading when the user is seated. The weight distribution of the user may be indicative of the seating posture of the user. For example, depending upon the sensed pressure difference between each of the sensors and which sensor reflects a higher relative pressure level, the electronics unit (or the mobile device) may process the information and alert the user or other party that the user is either leaning too far forward, leaning too far back, or is maintaining a correct posture.

In yet other variations, the pressure sensors in the support may be used in combination with other sensors that can collect biometric data of the user such as heart rate, respiration, body movement, etc.

BRIEF DESCRIPTION OF THE DRAWINGS

FIGS. 4A and 4B show top and bottom views, respectively, of the multi-layered support.

FIG. 5 shows a chart illustrating experimental results comparing pressure measurements with variations of the multi-layered support.

FIG. 12 shows an example of a support which may have one or more sensors configured to detect any number biometric data from the user.

DETAILED DESCRIPTION OF THE INVENTION

Generally, in a healthy individual, the presence of muscle mass and soft tissue usually functions to distribute and relieve pressure from bony protuberances of the body contacted against the underlying surface. However, when a patient is forced to lie on one portion of their body for extended periods of time, areas such as the sacrum or trochanter (or other portions of the body such as the heel, elbow, head, etc.) may compress a region of the skin and tissue between the protuberance and a contact region formed against the underlying surface.

A support assembly may be worn or used to support an individual who may be immobilized, e.g., such as sitting in a wheelchair, for extended periods of time to prevent the formation of pressure ulcers. Such a support assembly may be placed against and/or beneath particular regions of the body where pressure ulcers tend to form, e.g., sacrum, trochanter, ischium, head, elbow, heel, as well as any other region of the body where support is desired. Various features which may be incorporated or included into the support assemblies described herein may be seen in further detail in the following U.S. patent application Ser. No. 13/189,320 filed Jul. 22, 2011 (U.S. Pub. 2013/0019873); Ser. No. 13/407,628 filed Feb. 28, 2012 (U.S. Pub. 2013/0019881); Ser. No. 13/683,198 filed Nov. 21, 2012 (U.S. Pub. 2013/0112213); Ser. No. 13/693,691 filed Dec. 4, 2012 (U.S. Pub. 2013/0092175); Ser. No. 13/760,482 filed Feb. 6, 2013 (U.S. Pub. 2013/0180530); Ser. No. 13/784,035 filed Mar. 4, 2013 (U.S. Pub. 2013/0180531); Ser. No. 13/784,133 filed Mar. 4, 2013 (U.S. Pub. 2013/0174855); Ser. No. 13/784,215 filed Mar. 4, 2013 (U.S. Pub. 2013/0174856); Ser. No. 13/784,260 filed Mar. 4, 2013 (U.S. Pub. 2013/0174859); Ser. No. 13/945,684 filed Jul. 18, 2013 (U.S. Pub. 2013/0298918); Ser. No. 13/065,877 filed Mar. 30, 2011 (U.S. Pub. 2011/0239372); Ser. No. 13/973,840 filed Aug. 22, 2013; and Ser. No. 14/191,212 filed Feb. 26, 2014. Each of which is incorporated herein by reference in its entirety and for any purpose herein.

Figure 1A:
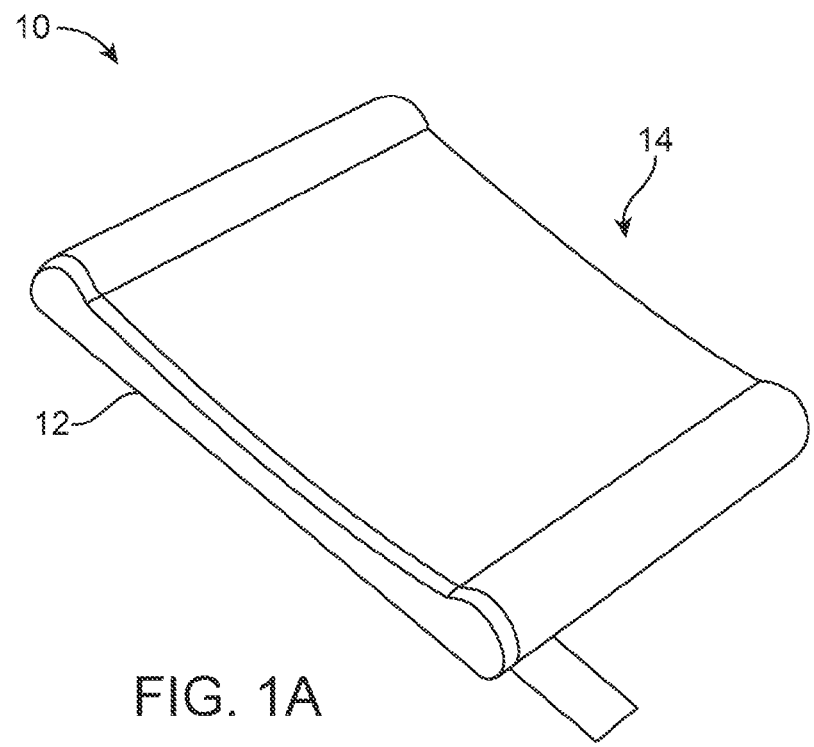
FIG. 1A shows a perspective view of a cushioning support assembly having a foam layer and a multi-layered support enclosed within a covering.
Figure 1B:
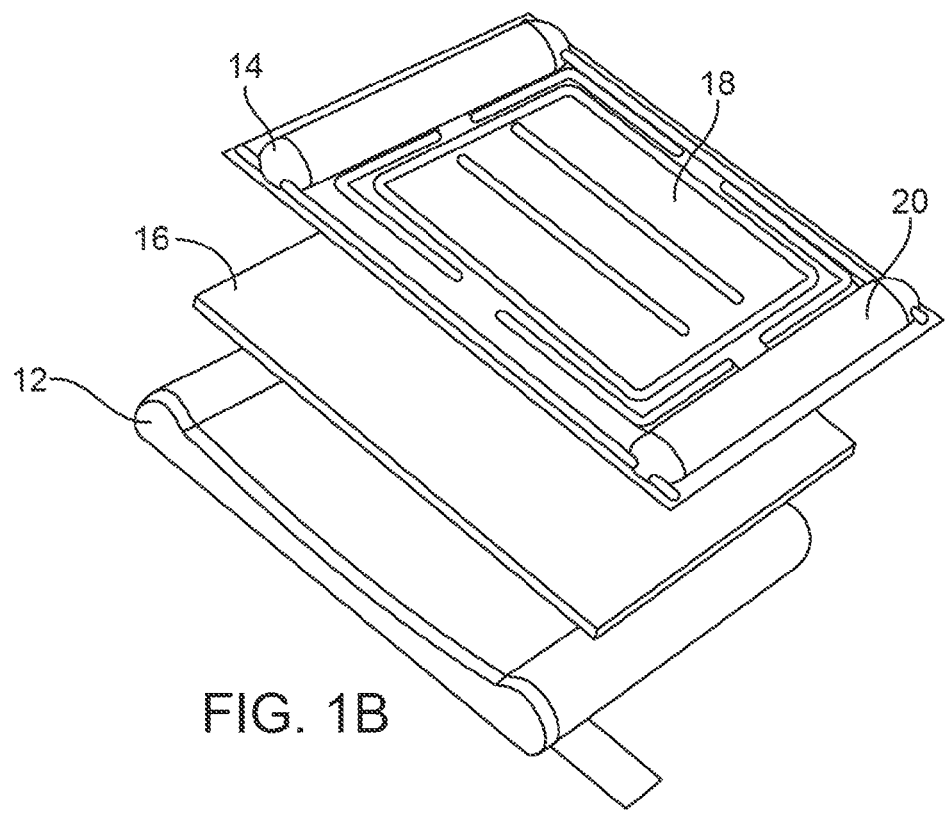
FIG. 1B shows an exploded assembly view of the individual foam layer and multi-layered support where the foam layer is positioned along the bottom surface of the multi-layered support or along the surface of the multi-layered support opposite to the contact surface.

One example of a supporting cushion is shown in the perspective view of FIG. 1A, which illustrates a cushion support 10 having a multi-layered cushioning support 14 contained within an enveloping cover 12. FIG. 1B shows an exploded assembly view of the multi-layered cushioning support 14 (described in further detail below) which may generally comprise several interconnected chambers configured to have a central support region and a surrounding support region 20 which are in fluid communication with one another. The multi-layered support 14 may be optionally filled with a gas (such as air) or liquid (such as water or mineral oil) or a combination of both. The multi-layered support 14 may also be sized in various dimensions suitable for placement under a patient body, e.g., 18 in.×20 in. for use as a cushion such as on a wheelchair. The multi-layered support 14 may also incorporate a relatively smaller secondary chamber 18 formed by an additional layer attached (such as by welding) upon the surface of the central support region 20 such that the region 20 surrounds this secondary chamber 18. The secondary chamber 18 may be filled by a volume of liquid, such as mineral oil, which is relatively more viscous than the gas or liquid filled within the central support region or surrounding support region 20. Moreover, this secondary chamber 18 may remain fluidly disconnected from the central support region and the surrounding support region 20.

Aside from the multi-layered support 14, an additional cushioning foam layer 16 may be positioned adjacent to the support 14 provided that this cushioning foam layer 16 is positioned along a bottom surface of the support 14, i.e., along a surface of the support 14 opposite from the secondary chamber 18. This is to allow for the multi-layered support 14 and secondary chamber 18 to come into direct contact against the patient's body without any other materials interfering (aside from the cover 12). The cushioning foam layer 16 may be comprised of, e.g., different density polyurethane foams, which can be fabricated into different sizes and thicknesses (e.g., 17 in.×19 in.×0.5 in.) depending upon the desired application. The foam layer 16 can be alternatively replaced by other cushioning designs such as a gel-type material, biasing springs, etc.

The cover 12 may envelope both the multi-layer support 14 and the foam layer 16 and may also be fabricated from various materials which can be breathable and waterproof. The surface of the cover 12 may also be made to have, e.g., an anti-skid surface, over its entire surface or along selective surfaces such as the bottom surface in contact with a platform. The cover 12 may be sized (e.g., 18 in.×20 in.×1.5 in.) similarly to the multi-layer support 14 and foam layer 16 which may both be inserted into the cover 12 through an opening defined along one of the edges of the cover 12. Additionally, while the individual layers 14, 16 may be maintained in their relative positioning by various mechanisms such as straps, fasteners, adhesives, etc., their relative positioning may also be maintained by the cover 12. Also, while the cover 12 may be placed atop the secondary chamber 18 for direct contact against the patient's body, the cover 12 is sufficiently thin enough so as not to interfere with the cushioning, support provided the layers 14, 16.

As previously discussed, the cushioning foam layer 16 is positioned along a bottom surface of the support 14, i.e., along a surface of the support 14 opposite from the secondary chamber 18, as shown in FIG. 1B, so that the secondary chamber 18 and multi-layer support 14 may be positioned into direct contact through the cover 12, if present, against the patient's body. Having the secondary chamber 18 of the support 14 placed into contact against the patient's body allows for effective pressure distribution throughout the support 14 while the foam 16 positioned beneath the support 14 (i.e., along the surface of the support 14 opposite of the secondary chamber 18 and away from the patient's body) provides for further cushioning support of the patient's body.

Figure 2A:
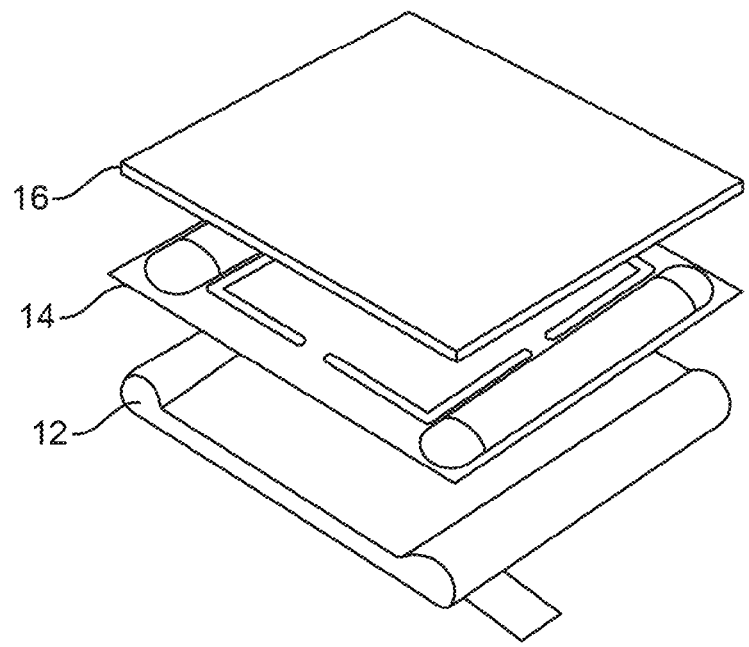
FIG. 2A shows an exploded assembly view of another variation where the foam layer is positioned upon the top surface or contact surface of the multi-layered support.
Figure 2B:
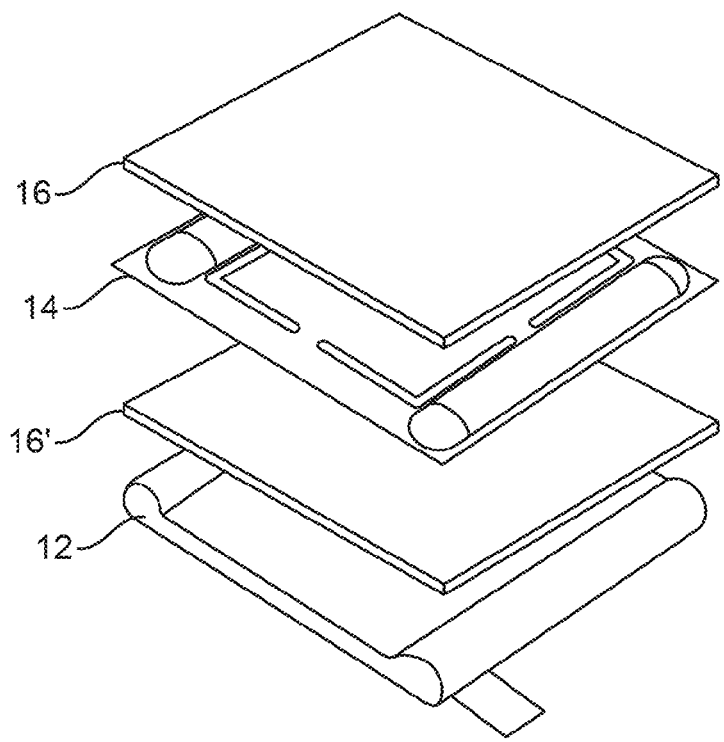
FIG. 2B shows an exploded assembly view of yet another variation where a first foam layer is positioned upon the top surface or contact surface as well as the bottom surface of the multi-layered support.

However, other variations of the cushioning support may include one example where the foam layer 16 may be positioned atop the multi-layer support 14, as shown in the exploded assembly view of FIG. 2A. In this variation, the foam layer 16 may be positioned along the same surface of the secondary chamber 18 such that the foam layer 16 comes into contact through the cover 12 with the patient's body. Another variation is shown in the exploded assembly view of FIG. 2B which is similar to the variation of FIG. 2A but with the addition of a second foam layer 16' positioned beneath the multi-layer support 14. In this case, the foam layer 16 and second foam layer 16' may be fabricated from the same or different materials and may be configured into the same or different dimensions depending upon the desired results.

Figure 3A:
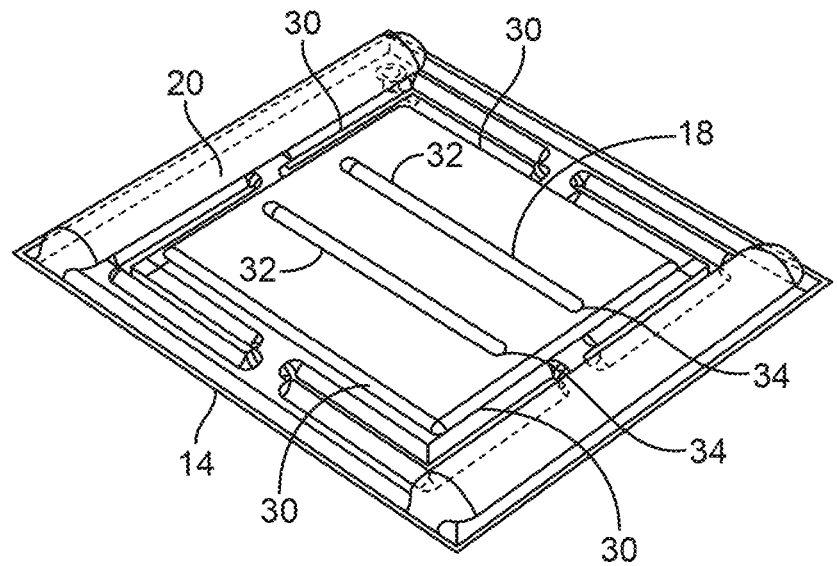
FIG. 3A shows a perspective view of the multi-layered support.
Figure 3B:
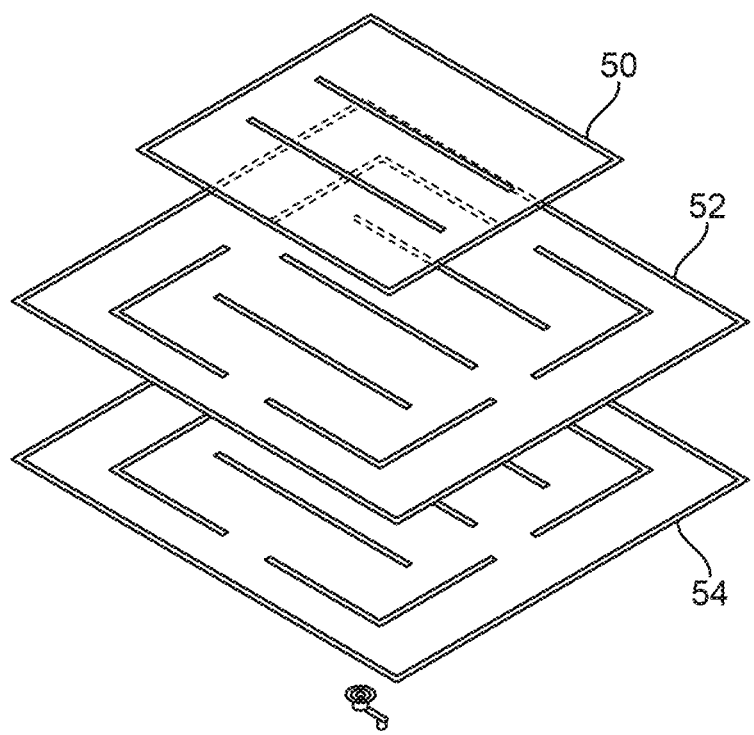
FIG. 3B shows an exploded assembly view of the individual layers forming the multi-layered support.

Turning now to the multi-layer support 14, a perspective view of one variation of the support is shown in FIG. 3A and an exploded assembly view of the individual layers forming the multi-layered support 14 is shown FIG. 3B. The secondary chamber 18 may be formed atop the support 14 via attachment along its edges 30 which may be welded, adhered, or otherwise attached. While the secondary chamber 18 may form a single chamber, one or more barriers or boundaries 32 may be formed along the secondary chamber 18 at least partially dividing the secondary chamber 18 into one or more sub-chambers which are fluidly connected to one another. The inclusion of the barriers or boundaries 32 may effectively slow or inhibit the flow of any fluids contained within the secondary chamber 18 from shifting to quickly such as when the patient adjusts their body position upon the support 14. The example shown in FIG. 3A illustrates a variation where the two barriers or boundaries 32 are formed in parallel along the secondary chamber 18 although in other variations, fewer than or more than two barriers or boundaries 32 may be formed in parallel configurations or various other configurations.

Moreover, the secondary chamber 18 may be formed to have an overall volume of, e.g., 0.6 liters, although this volume may be decreased or increased depending upon the desired results and the type of liquid contained within the chamber 18. This volume held within the secondary chamber 18 is less than the volume in the underlying support 14. This variation may contain, e.g., 0.6 liters of mineral oil, as the oil may help in reducing the pressure in combination with an underlying air layer contained within the remaining chamber of the support 14. When in use, the oil layer within the chamber 18 may be cradled by the underlying air chamber to prevent any potential "edge effects" associated with fluid interfaces. Moreover, the inclusion of the oil layer within the chamber 18 may also facilitate the delivery of cooling or heating therapy against the patient body as oil may be cooled or heated by any number of passive or active methods. Additionally and/or alternatively, the air within the remaining chamber may also be cooled or heated by any number of methods as well. However, because oil has a relatively higher specific heat than air, the oil layer within the chamber 18 may retain heat for longer periods of time.

As shown in the exploded assembly view of FIG. 3B, each of the individual layers forming the multi-layered support 14 may be seen. A first layer 50 forming the top layer of the secondary chamber 18 may be formed as a sheet having a thickness (e.g., 0.020 in.) made from various polymeric materials, e.g., polyvinyl chloride (PVC). The first layer 50 may be formed to have various dimensions (e.g., 13 in.×12 in.) which are shorter than the second layer 52 upon which the first layer 50 may be attached. The second layer 50 and third layer 54 may also be formed as sheets having a thickness (e.g., 0.010 in.) similarly made from various polymeric materials such as PVC. Each of the layers 52, 54 may be similarly sized to have various dimensions (e.g., 20 in.×18 in.) and may be attached to one another along seams formed around the periphery of the layers 52, 54 as well as along various locations between the sheets. However, while the second and third layers 52, 54 are attached to one another, the first layer 50 may remain attached only to the underlying second layer 52.

The top and bottom views of the multi-layer support 14 are shown in further detail in respective FIGS. 4A and 4B. As illustrated in FIG. 4A, while the first layer 50 may be welded or otherwise attached to the second layer 52 around the periphery of the first layer 50 along attachment 30, the formation of the barriers or boundaries 32 may also be seen formed between the first layer 50 and second layer 52. As previously described, the barriers or boundaries 32 may be formed at least partially between the respective layers 50, 52 such that fluid passageways 34 are formed between each of the sub-chambers to allow for the passage of fluid throughout the secondary chamber 18. The fluid passageways 34 may be formed to have a width of e.g., 1.5 in. or more.

As illustrated in the bottom view of FIG. 4B, further details may be seen between the second layer 52 and third layer 54. The second and third layers 52, 54 may be attached or otherwise welded to one another to divide the support into sub-chambers which remain in fluid communication with one another. In this variation, a central chamber 40 may be defined along a central portion of the support 14 while a peripheral chamber 42 may be formed to surround the central chamber 40. One or more barriers or boundaries 36 may be formed between the central chamber 40 and the surrounding chamber 42 by welding or otherwise attaching portions of the second and third layers 52, 54 to one another. The barrier or boundary 36 may be formed to follow the outer periphery of the support 14 (e.g., having a width ranging from 2 in. to 3 in.) while also defining one or more fluid passageways 44 (e.g., having a width of 2 in. or more) between the central chamber 40 and the surrounding chamber 42. The fluid passageways 44 may be formed along each of the sides of the barrier or boundary 36 to allow for the passage of air between the central chamber 40 and surrounding chamber 42.

With the multiple layers of support as well as the use of multiple sub-chambers, the gas or liquid within the support 14 may become displaced (within each of the layers) when a portion of the patient's body is positioned thereupon. At least some of the air in the central chamber 40 may displace through one or more of the fluid passageways 44 into the peripheral chamber 42 to one or more regions adjacent to the portion of the body and cause the sides of the support 14 (e.g., the surrounding peripheral chamber 42 and any portions of the central chamber 40 adjacent to the body portion) to lift up slightly relative to the portion of the support 14 which is in contact with the body portion. Some of the oil or liquid within the secondary chamber 18 may also displace away from the body portion through fluid passageways 34 but remains within the secondary chamber 18.

As the peripheral chamber 42 lifts relative to the portion of the support 14 which is in contact with the body portion, the displaced liquid or gas may also increase the surface area of the support 14 contacting against and supporting the portion of the body resulting in a cradling effect on the body portion. For example, if the patient's hip were placed upon the support 14, the displaced air within the central chamber 40 (and/or the oil in the secondary chamber 18) may become displaced immediately below the contacted hip. The displaced liquid or gas from the central chamber 40 may flow into the adjacent peripheral chamber 42 which may rise slightly relative to the central chamber 40 such that the hip becomes cradled by the support 14. Additionally, the overall surface area of the support 14 contacting against the hip may increase and the support 14 may lift up not only the hip but the regions of the patient's body adjacent to the hip.

The central chamber 40 may also have one or more barriers or boundaries 38 defined along the central chamber 40 as well. Although three boundaries 38 are shown in parallel with one another, fewer than or greater than three boundaries 38 may be formed. Each of the barriers or boundaries 36, 38 as well as the passageways 44 may allow for fluid communication throughout the central chamber 40 and surrounding chamber 42 in a controlled manner. Additionally, the third layer 54 may also incorporate a valve 46 to allow for the passage of air into the support 14. The volume of the secondary chamber 18 may remain fluidly disconnected from the remainder of the support 14 since the secondary chamber 18 may be filled with a volume of mineral oil, e.g., 0.6 liters.

EXPERIMENTAL RESULTS

In determining, the efficiency of the embodiments described herein, several experiments were conducted to measure the skin interface peak pressure values (mmHg)

from a patient (24 year old male, 155 lbs) sitting upon various cushioning supports placed within a conventional wheelchair. The resulting pressures generated by the patient were then measured and compared as shown in the following Table 1:

TABLE 1

Measured pressure values.

| Test | Peak Pressure (mmHg) | | | | % Increase in Avg. Peak Pressure Relative to Multi-Layered Support Having 1.5 × 17 × 19 Thick Foam on Bottom |
|---|---|---|---|---|---|
| | #1 | #2 | #3 | Average | |
| 1 (No cushon) | 200 | | | 200 | 59% |
| 2 (Multi-layered support with 1.5 in. × 17 in. × 19 in. foam layer along bottom surface) | 84.84 | 81.79 | 78.64 | 81.8 | 0% |
| 3 (Gel layer with foam layers along top and bottom surfaces) | 128.3 | 102.75 | 108.29 | 113.1 | 28% |
| 4 (Multi-layered support with 0.5 in. × 17 in. × 19 in. foam layer along bottom surface) | 81.51 | 91.37 | 84.94 | 85.9 | 5% |
| 5 (Multi-layered support with 0.5 in. × 17 in. × 19 in. foam layer along top surface) | 105.11 | 107.29 | 101.39 | 104.6 | 22% |
| 6 (Multi-layered support with 0.5 in. × 17 in. × 19 in. foam along top and bottom surfaces) | 102.51 | 106.81 | 101.5 | 103.6 | 21% |

FIG. 5 shows the corresponding pressure maps generated by the patient body along each of the tested embodiments shown above in Table 1.

As shown in the Table above, tests were performed with several different support configurations and multiple readings were compiled and averaged for each support configuration. The embodiment of the multi-layered support 14 having the foam layer 16 (having a thickness of 1.5 in.) positioned beneath the support 14 is shown in Test 2 which indicates a 0% for a baseline pressure measurement. The peak pressure of 200 mmHg with no cushioning support at all was measured in Test 1 correlating to a 59% increase in the average peak pressure measured relative to the embodiment of Test 2. The higher the percentage increase in measured peak pressure indicates a corresponding drop in the cushioning support provided.

Test 3 was performed utilizing a conventional Coccyx Gel/Foam Cushion (Nova Ortho-Med, Inc.) typically used in wheelchairs for comparison. The average measured peak pressure correlated to a relative 28% increase which corresponds to a drop in cushioning support relative to the embodiment of Test 2. These results indicate that the cushioning support provided by the embodiment described for Test 2 provides for a significant pressure drop and increase in cushioning support compared to no support at all and also compared to a conventional cushioning support.

The remaining tests were performed with a multi-layered support 14 having a foam layer 16 which was relatively thinner (having a thickness of 0.5 in. compared to a thickness of 1.5 in.) positioned relative to the support 14. Test 4 was performed using the relatively thinner foam layer 16 positioned similarly along a bottom surface of the support 14 correlating to a relative 5% increase in average peak pressure which corresponds to a drop in cushioning support relative to the embodiment of Test 2.

Test 5 was performed using the relatively thinner foam layer 16 positioned along a top surface of the support 14 which correlated to a relative 22% increase in average peak pressure which also corresponds to a drop in cushioning support relative to the embodiment of Test 2. Test 6 was performed using the relatively thinner foam layer 16 positioned along both a top and bottom surface of the support 14 which correlated to a relative 21% increase in average peak pressure which also corresponds to a drop in cushioning support relative to the embodiment of Test 2. These test results in particular indicate the desirability of positioning the foam layer 16 along the bottom surface of the support 14 away from the patient body so as not to dampen the supportive effects of the secondary chamber 18 and the overall support 14. Additionally, an increase in the thickness of the foam layer 16 also provides for an increase in cushioning support.

Variations of the multi-layered support described herein may be used for supporting other regions of the body. For instance, an embodiment for supportive use of the patient's heels may similarly utilize the same features. Such a variation may be designed to have dimensions scaled appropriately for supporting a heel (e.g., 10 to 13 in. width, 28 to 35 in. length, and 2 to 8 in. height) such that the support may be positioned below the calf when the patient is lying upon a bed so that the heel is lifted off the surface of the bed. The heel protector can also be designed to have an incline to give a gentle slope.

Using the multi-layered support or any of the other variations described herein, the support may be integrated with one or more sensors and/or electronics which enable the support to communicate, for instance, with a remote device to allow for the monitoring of various parameters such as pressure, sitting duration, etc. or various physiological parameters of the user.

The integrated sensing and/or monitoring of the support may thus be configured to sense specific parameters such as the user's sitting duration where the support and/or remote device may be configured to provide a warning or alert the user if duration is too long, i.e., at or above a predetermined sitting duration threshold. Additionally and/or alternatively, the support and/or device can be configured to sense for improper posture of the user and to provide a warning or alert to the user if their posture needs correction. Additionally and/or alternatively, the support and/or device can also be configured to sense physiological parameters such as breathing rate, heart rate, etc., and to update the user on the biometrics. The warning or alert on the remote device may comprise any visual (e.g., lights, flashes, etc.), auditory (alarms, music, messages, etc.), or haptic (e.g., vibration, etc.) alerts or a combination thereof. Also, the support and/or device can also be configured to provide real-time or historical data to the user such as the amount of calories burned by the user while sitting upon the support.

Figure 6:
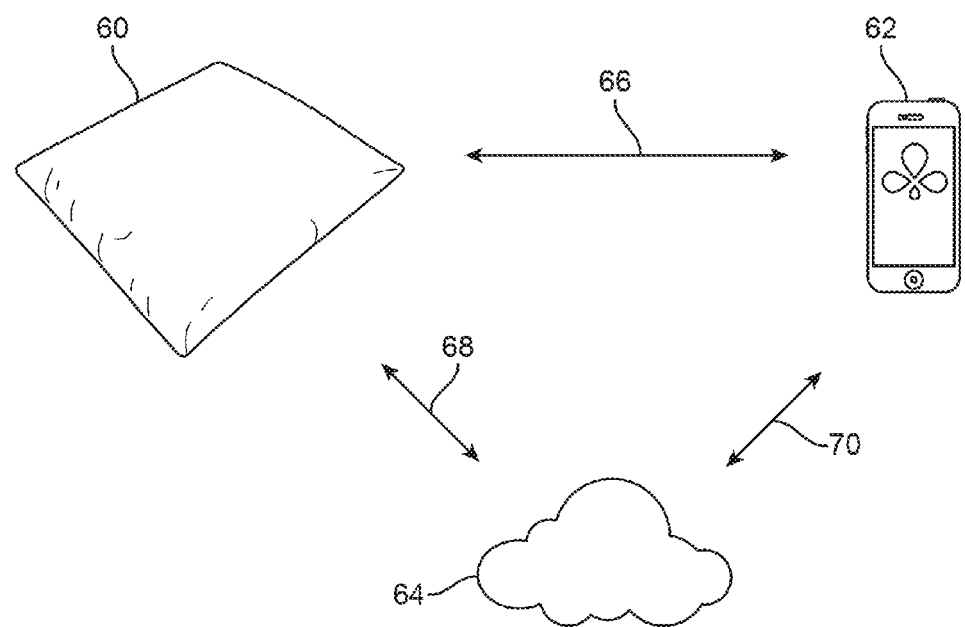
FIG. 6 shows an illustrative example of a support and a mobile device in communication with one another directly or through a network.

FIG. 6 shows an illustrative example showing support 60 and a mobile device 62 (e.g., smart phone, tablet, PDA, laptop, etc.) which is transportable and readily programmable (such as via an application, standard software, etc.) in communication 66 with one another. The mobile device 62 may comprise a standalone device designed specifically for use with the support 60. However, in the event that the mobile device 62 comprises a programmable device such as a smart phone (e.g., iPhone®, Android®, etc.), the user's own mobile device 62 may be used and specialized software code (e.g., in the form of downloadable applications) may be downloaded to the device 62 to program the device 62 to communicate with the support 60 as well as process information, as described in further detail herein.

The communication may occur via a wired cable or wirelessly through any number of wireless protocols (e.g., Bluetooth®, 802.11, GSM or CDMA cellular protocols, RF, NFC, etc.). Additionally and/or alternatively, communication 68, 70 may occur between the support 60 and mobile device 62 through the internet 64 or other network (e.g., LAN, WAN, etc.). While a mobile device 62 is illustrated and described, conventional computer systems or stationary servers may also be utilized instead for communication with the support 60.

In the event that the support 60 and mobile device 62 communicate through the internet 64, any or all of the monitored data (which may also be stored in local memory within the support 60) may be uploaded to a remote cloud storage location, if so desired. This data may be processed locally within the electronics integrated with the support 60 or via the mobile device 62 or a remote computer for display or tracking by the user. Optionally, the user's data as well as the data from multiple users may all be uploaded and compared for display to one or more the individual users. For instance, one individual user may create a group of other users authorized by this individual for sharing and comparing one another's data and/or for feedback by the group of users.

Figure 7:
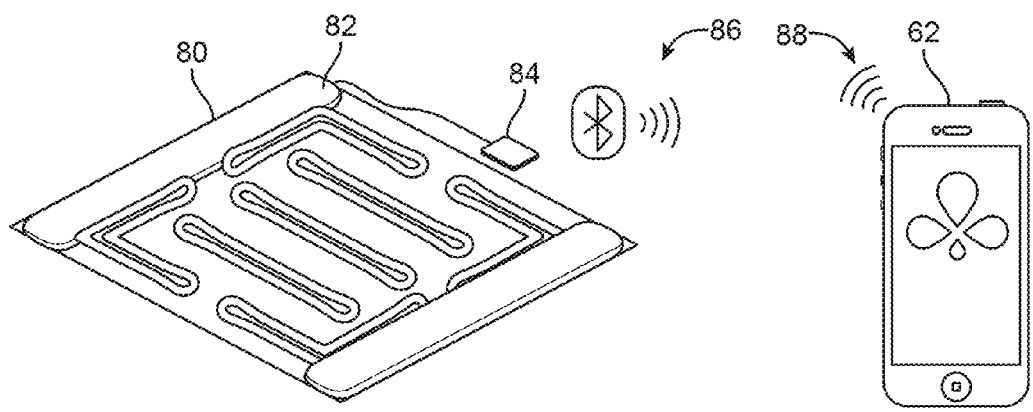
FIG. 7 shows an illustration of one variation of a support having a sensor integrated within the support and electrically coupled to an electronics unit which may wirelessly transmit information received from the sensor for receipt by the mobile device.

FIG. 7 shows another illustration of one variation of the system where a support 80 (shown without a covering for clarity) is illustrated having a sensor 82 integrated within the support 80 and electrically coupled to an electronics unit 84 (e.g., microprocessor, memory, antenna, power supply, amplifier, filter, etc.) which may wirelessly transmit 86 (via any of the protocols or methods described herein) information received from the sensor 82 for receipt 88 by the mobile device 62. The electronics unit 84 may comprise the microprocessor and/or one or more of the other electronic components while the sensor 82 may comprise any number of sensors such as an air pressure sensor configured to measure an internal bladder pressure within the support 80. Alternatively, the sensor 82 may comprise a capacitive or resistive pressure or force sensor which may be, for instance, sandwiched between bladder and foam and/or below the bladder or above the bladder, etc.

In one example for utilizing the sensor, the support may be used to track the duration of time that the user has been sitting upon or against the support and to optionally provide an alert either to the user or to a designated third party (e.g., relative, friend, care provider, doctor, nurse, etc.) via the mobile device (or another designated device) if the user has been sitting in one position for too long. Once the support 80 is loaded with weight as is the case when the user sits on it, the pressure inside the bladder chamber increases. Typically the unloaded bladder may have an internal bladder pressure ranging from, e.g., 0 to 0.2 psi, and when a person of typical weight sits upon the support 80, the pressure may increase up to, e.g., 0.2 to 1 psi, depending on the weight of the person. This change in pressure is instantaneous.

The sensor 82 may be connected to the fluid chamber of the bladder and this pressure reading is measured and converted into a voltage by the electronics unit 84. The sensor reading can be transmitted remotely via different wireless communication modes (as described herein) or wired communication to the mobile device 62.

Figure 8:
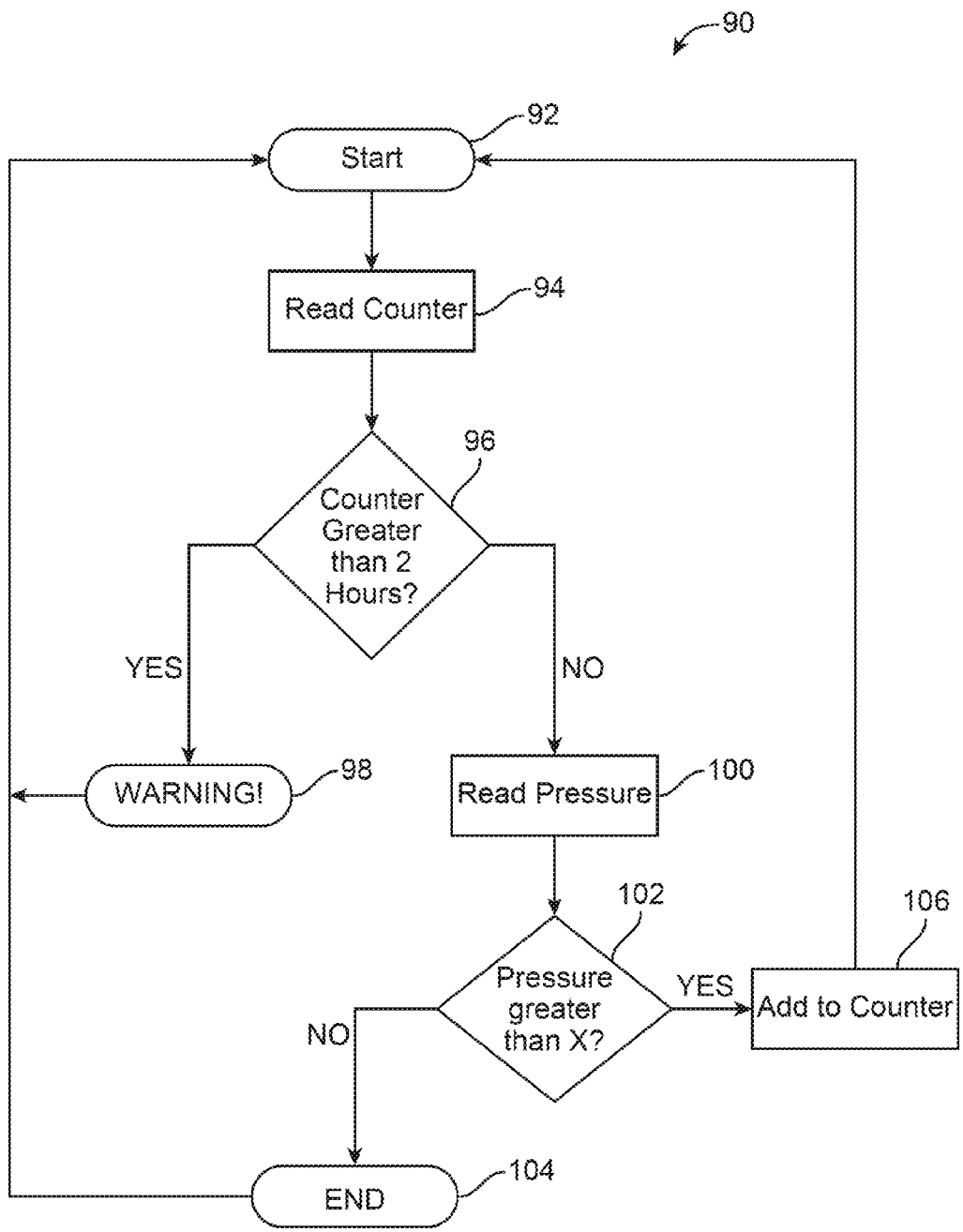
FIG. 8 shows an algorithm for monitoring or tracking a sitting duration time of a user upon a support.

This may be illustrated in part by the algorithm 90 shown in FIG. 8 which, in this example, may be configured for monitoring or tracking a sitting duration time of the user upon the support 80. The microprocessor contained within the electronics unit 84 may be programmed to start 92 automatically once the user sits upon the support 80 or upon actuation by the user or other party such as a care provider. As the pressure rises within the bladder chamber of the support 80, the sensor 82 may begin detecting the pressure increase and the microprocessor within the electronics unit 84 may begin a counter 94 which tracks the time so long as the pressure reading is maintained at its elevated level. The sensing of a constant elevated pressure level without any significant pressure fluctuations may indicate that the user has not shifted their position upon the support 80 and hence the counter 94 may continue to track the time. If the counter 94 exceeds a predetermined period of time, e.g., 2 hours (although any predetermined period of time may be programmed), the microprocessor may be programmed to make a decision 96. A "YES" signal may be indicated prompting the electronics unit 84 to transmit a warning or alert 98 to the mobile device 62 or other designated device or computer. However, if a "NO" signal is indicated, then the pressure may be read again 100 and the microprocessor may be further programmed to make another decision 102 based on the pressure reading.

If the measured pressure is less than a predetermined level, e.g., less than 1 psi, then a "NO" signal may be indicated which may correspond to the user shifting upon the support 80 or maintaining a suitable position upon the support 80 and the routine may end 104 and start again to continue the monitoring process. However, if the measured pressure is greater than the predetermined level, e.g., greater than 1 psi, then a "YES" signal may be indicated which may signal the microprocessor to add to counter 106 and the routine may start again to continue monitoring of the user sitting duration. When such a pressure increase is detected, the counter 106 may be updated to keep track of the duration for which the user is sitting or resting upon the support 80.

Figure 9:
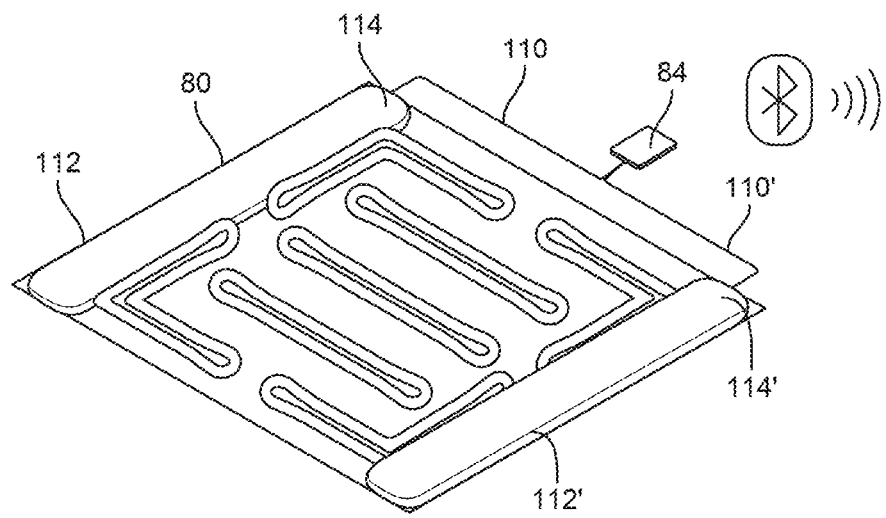
FIG. 9 shows an illustrative example of a support having a fluid chamber separated into at least two separate chambers which are each in communication with its own respective pressure sensor.

Another variation of the system may include a support 80 which may be configured to sense for improper posture by the user and to warn and/or alert the user if their posture needs correction. An example is shown in the perspective view of FIG. 9 which shows support 80 having a fluid chamber which is separated into at least two separate chambers, e.g., first chamber 112 and second chamber 112', which are each in communication with its own respective pressure sensor, e.g., first sensor 114 and second sensor 114'. While two separate chambers 112, 112' and two pressure sensors 114, 114' are shown, multiple chambers and pressure sensors may be used if desired. Each of the sensors 114, 114' may be connected via respective wires or cables 110, 110' to an electronics unit 84 which may be used to monitor and process the data received from each of the sensors.

Figures 10A, 10B, 10C:
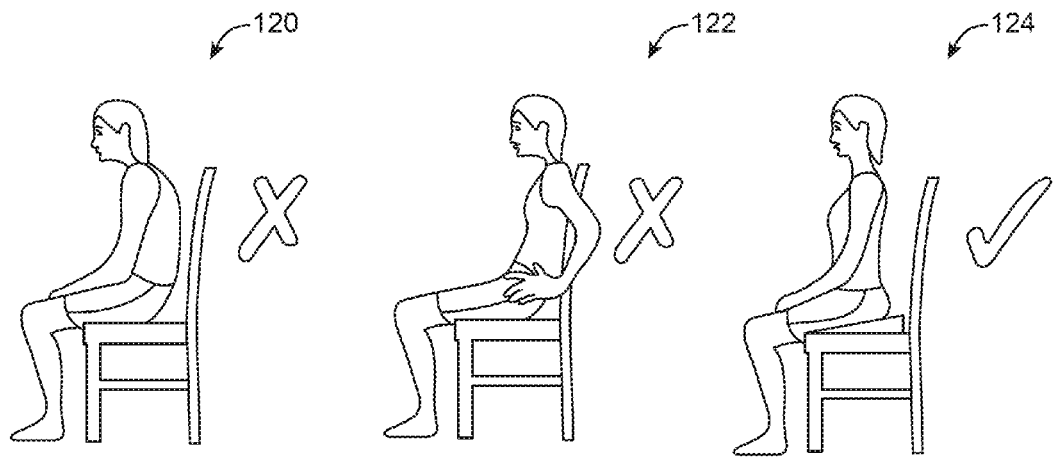
FIGS. 10A to 10C show examples of user posture which may be determined by the support.

Regardless of the number of chambers and sensors, the sensors may be positioned on opposing sides of the support 80 and at locations sufficiently distanced from one another so that the weight distribution of the user may be reflected by the different sensors to indicate differential loading when the user is seated. The weight distribution of the user may be indicative of the seating posture of the user. For example, depending upon the sensed pressure difference between each of the sensors and which sensor reflects a higher relative pressure level, the electronics unit 84 (or the mobile device 62) may process the information and alert the user or other party that the user is either leaning too far forward 120 as shown in FIG. 10A, leaning too far back 122 as shown in FIG. 10B, or is maintaining a correct posture 124 as shown in FIG. 10C.

Figure 11:
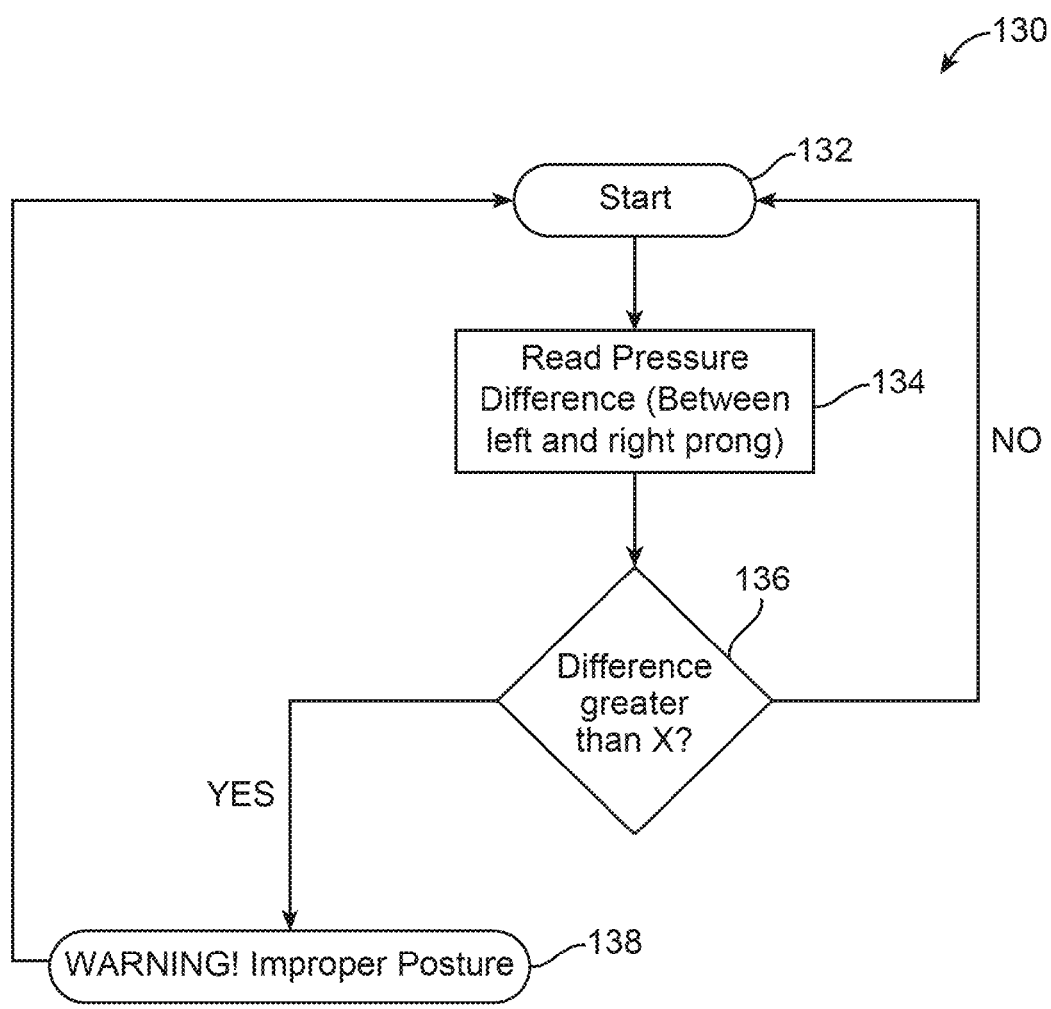
FIG. 11 shows an algorithm for posture detection.

FIG. 11 shows an example of an algorithm 130 for posture detection. This variation shows an example where the support 80 is separated into at least two separate fluid chambers each with a separate pressure sensor integrated into the fluid chambers. These two separate chambers may be located on both sides of a centerline defined by the support 80. The user may sit upon the support 80 so that the fluid chambers are positioned anteriorly and posteriorly relative to the patient's body and the algorithm 130 may start within the electronics unit 84. When the user is sitting correctly with uniform pressure on both sides of their hips, the pressure inside of both of the chambers is uniform leading to either similar readings of pressures if two sensors are used or a differential reading close to a predetermined baseline if one differential sensor is used (e.g., one reading is +ve while other is −ve thus canceling each one out).

In the case of the user leaning towards one side, the pressure in the chamber where the person is leaning towards is higher than the pressure in the other chamber, as shown in step 134, leading to a differential reading. If this differential reading is greater than a predetermined level, e.g., greater than 0.05 psi, as shown in step 136, then a "YES" signal may be indicated which can actuate an alert 138 to the user to correct their posture. If the differential reading is less than the predetermined level, then a "NO" signal may be indicated which allows the monitoring algorithm 130 to continue monitoring the user.

While this variation may be specific for a support 80 having two fluid chambers, other variations may utilize additional fluid chambers in the support 80 with additional corresponding pressure sensors for detecting and monitoring user posture along other planes (e.g., side-to-side) in addition to the user leaning forwards or backwards.

In yet other variations, the pressure sensors in the support 80 may be used in combination with other sensors that can collect biometric data of the user such as heart rate, respiration, body movement, etc. Alternatively, the pressure sensors themselves can be configured to also detect and monitor other biometric data such as heart rate, respiration, body movement, etc. For example, if the support 80 were used in a vehicle such as a plane, car, or truck for long distance transportation (e.g., pilots, truck drivers, etc.), the support 80 can potentially warn the user if they start falling asleep. This alert can be a function of the heart rate, respiration rate, and macro/micro motions of the user's body.

FIG. 12 shows an example of a support 80 which may have one or more sensors 140, 142 which may be integrated into the support 80. These one or more sensors 140, 142 may be configured to detect any number biometric data from the user sitting upon the support 80. Such parameters, such as heart rate 144 and/or respiration rate 146 may be received by the electronics unit 84 for processing and/or transmission to the mobile device 62 or other processor for monitoring and/or presentation to the user or other party.

Additionally and/or alternatively, the support 80 may also be configured to provide other functions such as temperature control of the support 80 and hence the user by active heating and/or cooling (e.g., via Peltier junctions, heating elements, fans, etc.) and the support 80 and electronics unit 84 may be appropriately sized for use in any number of applications and locations such as office chairs, wheelchairs, cars, airplanes, beds, etc.

The applications of the devices and methods discussed above are not limited to particular regions of the body such as the sacrum, trochanter, ischium, head, elbow, heel, etc. but may include any number of further applications. Modification of the above-described device and methods for carrying out the invention, and variations of aspects of the invention that are obvious to those of skill in the art are intended to be within the scope of the claims.

What is claimed is:

1. A monitoring system comprising:
    a support for supporting at least a portion of a user's body, wherein the support comprises a first layer and a second layer opposite the first layer, wherein the first and second layers define a central chamber and a peripheral chamber surrounding the central chamber, wherein the central chamber and the peripheral chamber are filled with a first gas or liquid, wherein the support further comprises a third layer, wherein the third layer is opposite both the first and second layers, wherein the second and third layers define an additional chamber, and wherein the additional chamber is filled with a second gas or liquid which is more viscous than the first gas or liquid;
    at least one pressure sensor in communication with the support; and
    an electronics unit in communication with the at least one pressure sensor,
    wherein the electronics unit is configured to transmit information relating to pressure sensed from the at least one pressure sensor to a remote device, and wherein the electronics unit and/or remote device is programmed to provide a warning or alert to inform the user that their posture is proper or improper when seated.

2. The system of claim 1, wherein the additional chamber is sized to contain a maximum volume which is less than a maximum volume of the central and peripheral chambers combined.

3. The system of claim 2 wherein the first gas or liquid comprises a volume of air.

4. The system of claim 2 wherein the second gas or liquid comprises a volume of oil.

5. The system of claim 2 further comprising a foam layer positioned adjacent to the first layer.

6. The system of claim 5 further comprising a cover configured to envelope the support and the foam layer.

7. The system of claim 1 wherein the electronics unit comprises a microprocessor.

8. The system of claim 1 wherein the electronics unit is further configured for wireless communication with the remote device.

9. The system of claim 1 wherein the remote device comprises a smart phone, tablet, PDA, laptop, or computer.

10. The system of claim 1 wherein the electronics unit and/or remote device is programmed to track a duration of time upon loading of the support.

11. The system of claim 10 wherein the electronics unit and/or remote device is programmed to provide a warning or alert to the user when the duration of time reaches or exceeds a predetermined level.

12. The system of claim 1 wherein the support comprises at least two fluid chambers separated from one another, each fluid chamber in communication with a corresponding pressure sensor which are in communication with the electronics unit.

13. The system of claim 12 wherein the electronics unit and/or remote device is programmed to determine a pressure differential between the fluid chambers and to provide a warning or alert if the pressure differential exceeds a predetermined level.

14. The system of claim 1 wherein the pressure sensor is further configured to detect and/or monitor one or more biometric parameters comprising heart rate, respiration, or body movement.

15. The system of claim 1 further comprising at least one biometric sensor in communication with the electronics unit and configured to detect and/or monitor one or more biometric parameters comprising heart rate, respiration, or body movement.

16. A method of monitoring use of a support, comprising:
providing a support for supporting at least a portion of a user's body, wherein the support comprises a first layer and a second layer opposite the first layer, wherein the first and second layers define a central chamber and a peripheral chamber surrounding the central chamber, wherein the central chamber and the peripheral chamber are filled with a first gas or liquid, wherein the support further comprises a third layer, wherein the third layer is opposite both the first and second layers, wherein the second and third layers define an additional chamber, and wherein the additional chamber is filled with a second gas or liquid which is more viscous than the first gas or liquid;
sensing a pressure within the support via at least one pressure sensor when the portion of the user's body is positioned upon the support; and
transmitting information relating to the pressure sensed by the at least one pressure sensor to a remote device via an electronics unit in communication with the at least one pressure sensor, wherein the electronics unit and/or remote device is programmed to provide a warning or alert to the user to indicate that their posture is proper or improper when seated.

17. The method of claim 16, wherein the additional chamber is sized to contain a maximum volume which is less than a maximum volume of the central and peripheral chambers combined.

18. The method of claim 17 further comprising providing a foam layer positioned adjacent to the first layer such that the foam layer is positioned away from the portion of the body.

19. The method of claim 18 further comprising providing a cover configured to envelope the support and the foam layer.

20. The method of claim 16 further comprising detecting and/or monitoring one or more biometric parameters of the user.

21. The method of claim 16 wherein sensing a pressure comprises sensing pressure from at least two pressure sensors in communication with a corresponding fluid chamber.

22. The method of claim 21 wherein the two pressure sensors are configured to optimize a sitting position of the user.

23. The method of claim 21 further comprising calculating a pressure difference between the at least two pressure sensors.

24. The method of claim 23 further comprising actuating a warning or alert to the user if the pressure difference exceeds a predetermined level.

25. The method of claim 16 wherein sensing a pressure comprises tracking a time duration of the portion of the user's body remaining upon the support.

26. The method of claim 25 further comprising actuating a warning or alert to the user if the time duration exceeds a predetermined level.

27. The method of claim 16 wherein transmitting information comprises wirelessly transmitting the information to the remote device.

28. The method of claim 27 wherein the remote device comprises a smart phone, tablet, PDA, laptop, or computer.

29. The system of claim 2, wherein the central chamber and the peripheral chamber are in fluid communication with one another.

30. The system of claim 29, wherein the first layer is attached to the second layer, and wherein the second layer is attached to the third layer.

31. The system of claim 1, wherein the warning or alert informs the user that they are leaning too far in a first direction when seated or leaning too far in a second direction when seated.

32. The system of claim 13, wherein the warning or alert indicates to the user to correct or maintain their posture when seated.

33. The method of claim 17, wherein the central chamber and the peripheral chamber are in fluid communication with one another.

34. The system of claim 33, wherein the first layer is attached to the second layer, and wherein the second layer is attached to the third layer.

35. The system of claim 34, wherein the electronics unit and/or remote device is programmed to determine a weight distribution of the user via the first and second pressure sensors, and wherein the electronics unit and/or remote device is programmed to provide a warning or alert to the user that their posture is proper or improper when seated based on the determined weight distribution.

36. The system of claim 35, wherein the first and second pressure sensors are positioned on opposing sides of the support.

37. The method of claim 21, wherein the electronics unit and/or remote device is programmed to determine a weight distribution of the user via the at least two pressure sensors, and wherein the electronics unit and/or remote device is programmed to provide a warning or alert to the user that their posture is proper or improper when seated based on the determined weight distribution.

38. The method of claim 37, wherein the warning or alert informs the user that they are leaning too far in a first direction when seated or leaning too far in a second direction when seated.

39. The method of claim 37, wherein the warning or alert indicates to the user to correct or maintain their posture when seated.

* * * * *